(12) United States Patent
Cotton

(10) Patent No.: US 11,452,642 B2
(45) Date of Patent: *Sep. 27, 2022

(54) ABSORBENT WOUND DRESSING FOR WRAPPING AROUND JOINTED LIMBS

(71) Applicant: BRIGHTWAKE LIMITED, Nottingham (GB)

(72) Inventor: Stephen Cotton, Nottingham (GB)

(73) Assignee: BRIGHTWAKE LIMITED, Nottingham (GB)

( * ) Notice: Subject to any disclaimer, the term of this patent is extended or adjusted under 35 U.S.C. 154(b) by 232 days.

This patent is subject to a terminal disclaimer.

(21) Appl. No.: 16/229,907

(22) Filed: Dec. 21, 2018

(65) Prior Publication Data

US 2019/0133831 A1    May 9, 2019

Related U.S. Application Data

(63) Continuation of application No. 13/263,619, filed as application No. PCT/GB2010/050608 on Apr. 8, 2010, now Pat. No. 10,195,087.

(30) Foreign Application Priority Data

Apr. 8, 2009  (GB) ...................... 0906056

(51) Int. Cl.
   *A61M 35/00*   (2006.01)
   *A61F 13/06*   (2006.01)
   (Continued)

(52) U.S. Cl.
   CPC ............. *A61F 13/06* (2013.01); *A61F 13/10* (2013.01); *A61F 13/064* (2013.01); *A61F 13/5323* (2013.01)

(58) Field of Classification Search
   CPC ......... A61M 35/00; A61F 13/00; A61F 13/20; A61F 13/15; A61F 5/00
   See application file for complete search history.

(56) References Cited

U.S. PATENT DOCUMENTS

| 1,845,630 A | 2/1932 | Scholl |
| 2,331,271 A | 10/1943 | Gilchrist |
(Continued)

FOREIGN PATENT DOCUMENTS

| EP | 0768071 A1 | 4/1997 |
| EP | 0769283 A1 | 4/1997 |
(Continued)

OTHER PUBLICATIONS

Great Britain Search Report for Patent Application No. GB0906056.7, dated Nov. 2, 2009.
(Continued)

*Primary Examiner* — Tatyana Zalukaeva
*Assistant Examiner* — Ilya Y Treyger
(74) *Attorney, Agent, or Firm* — Troutman Pepper Hamilton Sanders LLP (Rochester)

(57) ABSTRACT

A non-adhesive absorbent wound dressing (10) is suitable for application about a jointed limb. The wound dressing (10) has a first portion (20) adapted to conform to and wrap around an upper part of the limb, a second portion (30) adapted to conform to and wrap around a lower part of the limb, and a hinge portion (40) between said first portion (20) and said second portion (30), said hinge portion (40) in use lying adjacent to the joint of the limb. The wound dressing (10) also comprises a porous wound contact sheet (80) and a substantially liquid-impermeable backing sheet (90), the wound contact sheet (80) and the backing sheet (90) being bounded (50) together at their periphery and along lines that define a plurality of pockets (60) in both the first portion (20)

(Continued)

and the second portion (30), the pockets (60) containing absorbent material (70).

26 Claims, 1 Drawing Sheet

(51) Int. Cl.
| | | |
|---|---|---|
| *A61F 13/10* | (2006.01) | |
| *A61F 13/00* | (2006.01) | |
| *A61F 13/20* | (2006.01) | |
| *A61F 13/15* | (2006.01) | |
| *A61F 5/00* | (2006.01) | |
| *A61F 13/532* | (2006.01) | |

(56) References Cited

U.S. PATENT DOCUMENTS

| | | |
|---|---|---|
| 4,360,015 A | 11/1982 | Mayer |
| 4,401,113 A | 8/1983 | Incorvaia |
| 4,699,823 A | 10/1987 | Kellenberger et al. |
| 4,820,293 A | 4/1989 | Kamme |
| D307,184 S | 4/1990 | McConnell |
| 5,129,391 A | 7/1992 | Brodsky |
| 5,264,218 A | 11/1993 | Rogozinski |
| 5,437,621 A | 8/1995 | Andrews et al. |
| 5,538,500 A | 7/1996 | Peterson |
| 6,075,177 A | 6/2000 | Bahia et al. |
| 6,706,279 B1 | 3/2004 | Hazzi |
| 7,049,478 B1 | 5/2006 | Smith |
| 8,663,144 B2 | 3/2014 | Farrow |
| 2001/0039405 A1 | 11/2001 | Keuhn, Jr. et al. |
| 2005/0118383 A1 | 6/2005 | Cargill et al. |
| 2007/0093767 A1 | 4/2007 | Carlucci |
| 2007/0134301 A1 | 6/2007 | Ylitalo et al. |
| 2008/0039759 A1 | 2/2008 | Holm et al. |
| 2008/0312573 A1 | 12/2008 | Chappell |

FOREIGN PATENT DOCUMENTS

| | | |
|---|---|---|
| GB | 2350280 A | 11/2000 |
| GB | 2357286 A | 6/2001 |
| GB | 2375485 A | 11/2002 |
| GB | 2389794 A | 12/2003 |
| WO | 86/04811 A1 | 8/1986 |
| WO | 92005756 A1 | 4/1992 |
| WO | 00/01425 A1 | 1/2000 |
| WO | 0042957 A1 | 7/2000 |
| WO | 03/092755 A1 | 11/2003 |
| WO | 2004/073567 A1 | 9/2004 |
| WO | 2008149107 A1 | 12/2008 |

OTHER PUBLICATIONS

International Search Report for Patent Application No. PCT/GB10/50608, dated Oct. 4, 2010.

ABSORBENT WOUND DRESSING FOR WRAPPING AROUND JOINTED LIMBS

This application is a continuation of U.S. patent application Ser. No. 13/263,619, which is a national stage application under 35 U.S.C. § 371 from PCT Application No. PCT/GB2010/050608, filed Apr. 8, 2010, which claims the priority benefit of Great Britain Patent Application No. 0906056.7, filed Apr. 8, 2009, which are hereby incorporated by reference in their entirety.

The present invention relates to absorbent wound dressings. More particularly, the present invention relates to wound dressings that are adapted to be wrapped around wounds on or near jointed limbs.

Wounds on curved or irregularly-shaped parts of the body, such as jointed limbs, are particularly problematic to dress and manage. This is partly because most standard wound dressings are substantially planar and are therefore not adapted to cover highly contoured surfaces. As a result, many dressings fail in their purported ability to absorb exudate, maintain complete coverage of the wound area and prevent secondary bacterial infection.

Standard wound dressings can be cut or folded in an attempt to cover jointed limbs and to conform to the shape of the wound, but the requirement for handling before application to the patient inevitably compromises the sterility of the dressing itself. Indeed, the more irregular the wound, the greater amount of prior manipulation is required and the less wound coverage is achieved. Adhesive dressings are more effective at covering an irregularly shaped wound area such as a wound on a jointed limb because the adhesive retains the dressings in place. However, removal of such dressings often causes further wound trauma. In other known dressing designs a dressing sheet is made up of absorbent compartments that are designed to be cut or torn along predefined lines of weakness in order to adapt the dressings to different shaped wounds. However, these suffer from the same sterility problems as standard wound dressings.

Particular problems occur in the management of highly exuding wounds such as leg ulcers. Known forms of absorbent dressings may not conform effectively to the wound site and may not have a sufficiently high absorbtive capacity. As a consequence, frequent dressing changes may be required, with the possibility of increased trauma to the wound. Also, the absorbent material has a tendency to slump to the bottom of the dressing when wound exudate is absorbed, particularly where the wound dressing is relatively large and, in use, is disposed upright, as for example when applied to a leg ulcer.

There has now been devised an improved wound dressing which overcomes or substantially mitigates the above-mentioned and/or other problems associated with the prior art.

According to a first aspect of the invention, there is provided a non-adhesive absorbent wound dressing for application about a jointed limb, the wound dressing having a first portion adapted to conform to and wrap around an upper part of the limb, a second portion adapted to conform to and wrap around a lower part of the limb, and a hinge portion between said first portion and said second portion, said hinge portion in use lying adjacent to the joint of the limb;

wherein the dressing comprises a porous wound contact sheet and a substantially liquid-impermeable backing sheet, the wound contact sheet and the backing sheet being bonded together at their periphery and along lines that define a plurality of pockets in both the first portion and the second portion, the pockets containing absorbent material.

The dressing of the present invention is advantageous primarily because it can be applied securely to an irregularly-shaped jointed limb, with a smaller amount of manipulation than is required for standard dressings. This considerably reduces the chances of compromising dressing sterility and introducing a pathogenic contaminant. Once the dressing has been applied to the patient, the hinge portion in use lying adjacent to the joint of the limb and the generally flexible nature of the dressing allow the dressing to flex as the joint flexes. In this way, complete wound coverage is achieved throughout the whole range of free limb movement. This means that the patient can achieve mobility faster than if standard dressings were applied and mobility has been shown to improve blood circulation to the wound and improve wound healing. The absorbent material contained within the pockets is able to absorb wound exudate, and because the first and second portions are sub-divided into a plurality of pockets, the absorbed wound exudate is held within those pockets. This reduces the tendency of the absorbent material to slump to the bottom of the dressing under the influence of gravity, which would otherwise be a particular problem where the dressing is disposed, in use, in an upright configuration.

The dressing of the invention is further advantageous because it is able to absorb and contain large amounts of wound exudate. This reduces the number of dressing changes that are required, which in turn reduces both clinical costs and nursing time. As large amounts of fluid are absorbed, maceration of the wound is prevented and patient comfort is improved. Once the dressing has reached its capacity for absorbing fluid, it can be removed and replaced quickly, without causing further trauma to the wound site (which is a problem with most standard dressings).

The wound contact sheet is preferably a fluid-permeable material. The wound contact sheet may comprise a woven or non-woven fabric, formed of synthetic or natural materials. In a presently preferred embodiment, the wound contact sheet is a non-woven sheet formed from a blend of polyester and viscose fibres. The wound contact sheet may be perforated in order to expedite the transport of fluid. In a presently preferred embodiment of the invention, the wound contact sheet is formed with a regular array of perforations across its full extent. Such perforations may be circular or non-circular in shape, or irregularly-shaped, and typically have a size of from 50 µm to 10 mm, more commonly from 0.1 mm to 1.5 mm.

The backing sheet is impermeable to liquid, or substantially so, so that wound exudate is retained within the dressing, but is preferably vapour-permeable. The backing sheet may comprise a film of material. Suitable backing sheet materials include plastics, such as polyethylene and polyurethane. The backing sheet material may have a degree of elasticity.

The wound contact sheet and the backing sheet are preferably bonded together at the perimeter of each sheet and along lines extending from the perimeter of each sheet. Preferably the material of the wound contact sheet and the backing sheet includes a fusible component so that the bonds can be formed by the application of heat and pressure. For example, the fabric may be a non-woven fabric containing both fusible (such as polyester or polypropylene) and non-fusible (such as cellulose) fibres. In other embodiments, the bonding may be achieved by the use of adhesives, stitching, or any other method known in the art.

A plurality of internal recesses, described herein as pockets, are defined by bonds between the wound contact sheet and the backing sheet that extend across the dressing. The pockets may have any suitable shape. For example, the pockets may be generally square, rectangular or triangular, or may have a less regular shape, eg an irregular quadrilateral shape.

The absorbent material preferably comprises any material that absorbs liquid, such as wound fluid. Preferably, absorbent material substantially fills each pocket. The absorbent material is preferably formed into a sheet, mat or pad. The sheet, mat or pad of absorbent material is preferably shaped and dimensioned such that it occupies substantially the whole of the pocket within which it is contained.

The absorbent materials are typically those types commonly referred to as "superabsorbers" or "superabsorbent materials". Such materials are typically polymers that are capable of absorbing and retaining extremely large quantities of fluid relative to their own mass.

Typically, such materials absorb aqueous solutions through hydrogen bonding with the water molecule, and may absorb up to 200, 400, or 500 times or more their weight of fluid.

Amongst the most commonly used superabsorbent polymers are polyacrylates, ie salts of polyacrylic acid. For instance, the sodium salt of polyacrylic acid (cross-linked sodium polyacrylate) may be produced by the polymerization of acrylic acid blended with sodium hydroxide in the presence of an initiator.

Other superabsorbent polymers include polyacrylamide copolymer, ethylene maleic anhydride copolymer, cross-linked carboxymethylcellulose, polyvinylalcohol copolymers, cross-linked polyethylene oxide, starch-grafted copolymers of polyacrylonitrile, and others.

Another class of superabsorbent polymer that may be used in the invention is alginate, ie salts of alginic acid. Such material occurs naturally as a viscous gum that is abundant in the cell walls of brown algae, and commercial forms are extracted from seaweed. Alginic acid is a linear copolymer with homopolymeric blocks of (1-4)-linked β-D-mannuronate and its C-5 epimer α-L-guluronate residues, covalently linked together in different sequences or blocks.

Alginates that are particularly suitable for use in the present invention are calcium alginate and sodium alginate.

In presently preferred embodiments, the absorbent material has the form of a sheet, mat or pad. The sheet, mat or pad may be formed from an absorbent material, or the sheet, mat or pad may be of a material that does not itself absorb fluid (or which has a relatively low absorptive capacity) but which acts as a carrier for a superabsorbent material. For instance, particles of superabsorbent polymer may be entrapped in the sheet, mat or pad, which may be of formed from fibres of a synthetic or natural material, eg cellulose. Suitable materials include those available under the trade name GELOK from Gelok International Corporation P.O. Box 69, Pine Lake Industrial Park, Dunbridge, Ohio 43414-0069 USA.

The absorbent material may alternatively be of the form described in GB Patent Application No. 0905341.4, ie a laminate of a layer of absorbent material and a layer of reinforcing material. Such a laminate may be formed by ultrasonic welding of the layers together at a plurality of weld points.

Both the first portion and the second portion comprise a plurality of pockets. The first and second portions may differ in size and may comprise differing numbers of pockets. Each of the first and second portions preferably comprise at least three pockets, more preferably at least four. The number of pockets in each of the first and second portions is, however, preferably no more than ten, more preferably no more than eight.

Generally, the absolute and relative dimensions of the first and second portions of the dressing will depend on the particular part of the body to which the dressing is intended to be applied. For instance, for application about a knee or elbow joint, the first and second portions may be comparable in size, the ratio of the areas of first and second portions being less than 3:1 or less than 2:1. For application about a wrist or ankle joint, where the parts of the body to which the first and second portions are applied are substantially different in size (ie the forearm and hand, or the lower leg and foot), on the other hand, the first portion may be substantially greater in extent than the second portion. In such a case, the ratio of the surface areas of the first and second portions may be greater than 3:1 or greater than 4:1 or greater than 5:1.

A currently preferred embodiment of the dressing according to the invention is intended for application to the lower leg and foot, about the ankle joint. In such an embodiment, the first portion of the dressing is wrapped, in use, about the lower leg, and the second portion is wrapped around the foot. The hinge portion lies adjacent to the patient's heel.

The hinge portion between the first and second portions comprises a bonded area which extends across the dressing, from one point on the perimeter of the dressing to another. The hinge portion thus represents a fold line about which the first portion and the second portion can be folded towards one another.

In order to permit the first and second portions to be wrapped around the upper and lower parts of the limb to which the dressing is applied, the hinge portion is preferably of reduced dimension relative to the parts of the first and second portions adjacent to it. The first and second portions of the dressing may have the same overall width, or different overall widths, depending on the intended manner and site of application of the dressing. Where, as is most common, the hinge portion is of lesser width, the width of the hinge portion may be up to 75%, or up to 60%, or up to 50% that of the first and/or second portion.

The wound dressing is most preferably sterile so as not to introduce infective agents into the wound. Where the materials used are sensitive to heat, sterilisation methods using heat or pressure are not suitable. A more preferred method of sterilisation may be gamma irradiation or chemical sterilisation using agents such as ethylene oxide, both of which are widely used for the sterilisation of medical equipment. Preferably the wound dressing is packaged in a microorganism-impermeable container.

The wound dressing of the invention may also comprise a carbonised deodoriser or an anti-microbial material. A preferred form of antimicrobial material is silver. Such materials may be included as inner layers of a composite absorbent material.

It will be appreciated that the wound contact sheet may also absorb some wound fluid. The overall absorbing capacity of the dressing may therefore be somewhat greater than the absorbtive capacity of the absorbent material included within each pocket.

The dressing according to the invention may be any generally planar shape that is dimensioned and configured to conform to a jointed limb. Preferably the dressing is configured to conform to and wrap around any upper part of any limb, any lower part of any such limb, and any joint positioned between any such upper and lower parts.

In use, the wound contact sheet of the hinge portion preferably lies adjacent to the joint of a limb (eg an ankle). The hinge portion may also lie adjacent to a non-hinged part of the body or joint which is maintained in substantially static configuration, such as a knee joint held bent by an external brace. Preferably, the first portion is wrapped around the upper part of the limb (eg a lower leg), and the second portion is wrapped around the lower part of the limb (eg a foot).

In use, the dressing can be manipulated to adapt to the three-dimensional form of the part of the body to which it is applied. The dressing is preferably of sufficient dimensions that opposing edges may be wrapped around the limb to which the dressing is applied, and overlapped. The dressing according to the invention is preferably held in place using surgical tape, hook and loop fixation, or other type of fixative.

The present invention will now be described in greater detail, by way of example only, with reference to the accompanying drawings, in which.

Figure 1:
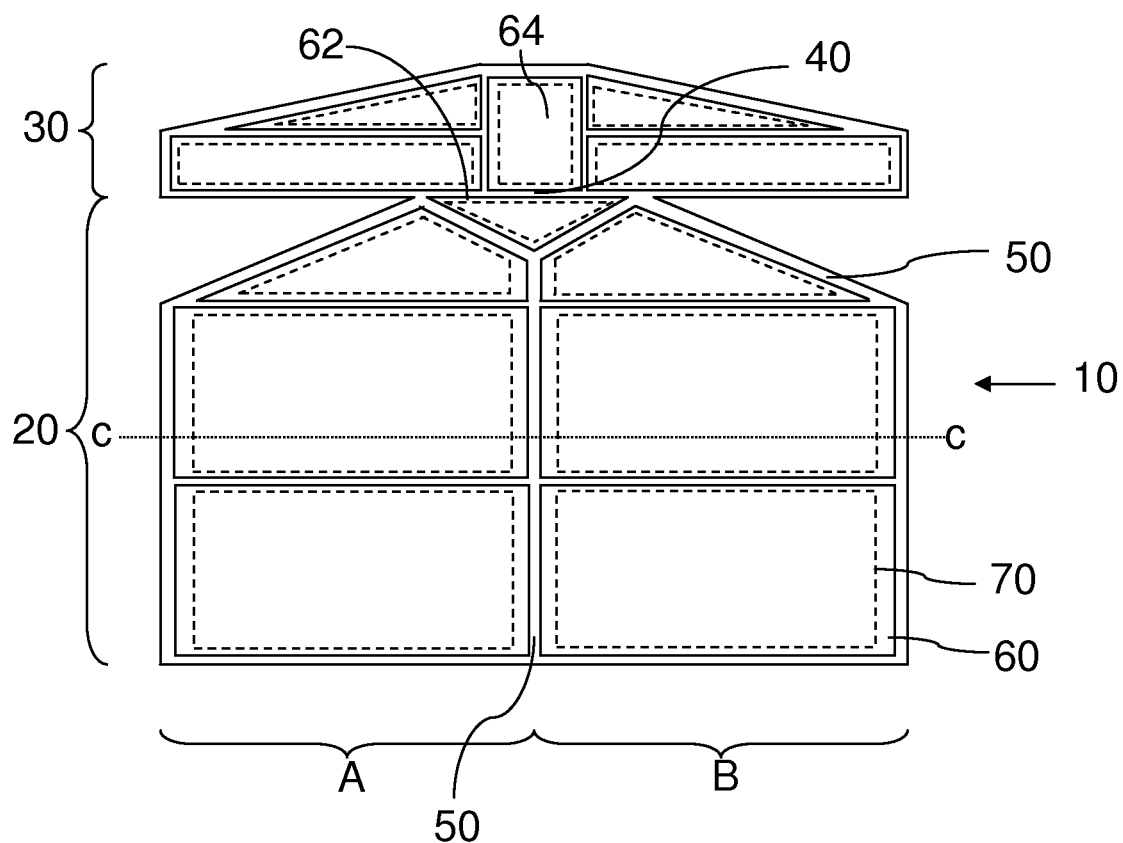
FIG. 1 shows a plan view of a dressing according to the invention.

Referring first to FIG. 1, an embodiment of the absorbent dressing according to the invention is shown and is generally designated 10. In this particular example the dressing has a shape suitable for application to the lower leg and foot, around an ankle joint.

The first portion of the dressing according to the invention is that generally designated 20. The second portion of the dressing according to the invention is that generally designated 30. A hinge portion 40 is positioned between the first and second portions 20, 30.

Figure 2:
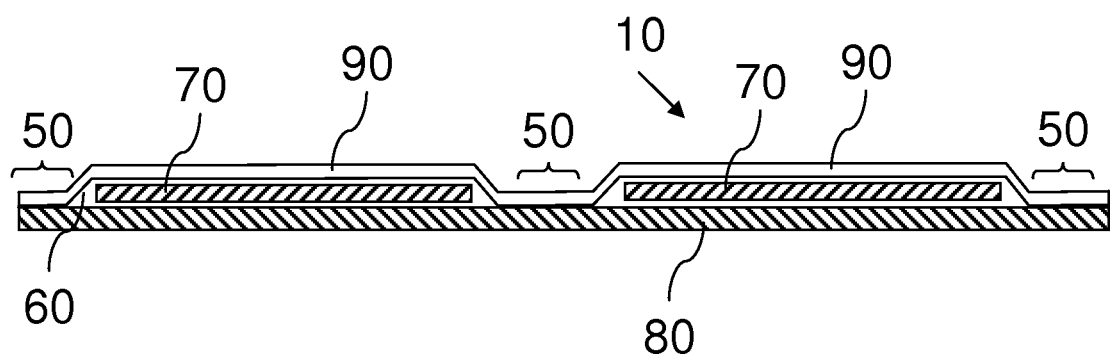
FIG. 2 shows, schematically and not to scale, a cross-sectional view on line "c-c" in FIG. 1.

The dressing 10 comprises a wound contact sheet 80, absorbent material 70 and a backing sheet 90, as shown in FIG. 2 which is cross-sectional view on line c-c in FIG. 1. The wound contact sheet 80 is formed of a non-woven blend of polyester and viscose, perforated across its whole extent with perforations of approximate size 1 mm. The backing sheet is a liquid-impermeable but vapour-permeable polyethylene film. The absorbent material 70 comprises a mechanically bonded cellulose pad containing particles of superabsorbent polymer.

The backing sheet 90 and the wound contact sheet 80 have the same overall shape and dimensions, and are superimposed on top of one another and bonded at the perimeter of the dressing and at a number of other positions within the periphery of the dressing, as indicated by the bonds 50. The bonds 50 are created by the application of heat and pressure, and define pockets 60. Each pocket contains absorbent material 70 which substantially fills each pocket 60. As can be seen from FIG. 1, the dressing 10 is symmetrical about its centre line (vertical as depicted in FIG. 1), the sides (denoted A and B) of each of the first and second portions 20,30 being formed as a pair of wings that can be wrapped around a limb to which the dressing is applied.

In the illustrated embodiment, the first portion 20 is formed with seven pockets 60, and the second portion with five pockets 60. Compartmentalisation of the first and second portions 20,30 into discrete pockets 60 is beneficial in that the absorbent material contained within each pocket 60 is less liable to slumping, which reduces the frequency with which the dressing must be changed, as well as improving its conformability and comfort for the patient.

The wound contact sheet 80 is permeable to fluid and is in contact with the wound. As such, the wound contact sheet 80 is able to transport wound exudate to the absorbent 70. The absorbent 70 may absorb many times, eg several hundred times, its own weight in wound exudate. The backing sheet 90 is impermeable to fluid and permeable to vapour, so that wound exudate is retained within the dressing 10 whilst vapour is allowed to escape. The materials of the dressing 10 are flexible and therefore the dressing 10 can be adapted to conform to and wrap around a jointed limb.

The embodiment of the dressing 10 depicted in the drawings is dimensioned and configured for application to a patient's lower leg and foot. In use, the dressing 10 is positioned such that the hinge portion 40 is located adjacent the patient's heel. The wings of the first portion 20 are then wrapped around the patient's lower leg (calf) and overlapped, and the wings of the second portion 30 are wrapped around the patient's foot and overlapped. The dressing 10 may then be secured by means of surgical tapes or the like. In alternative embodiments, the dressing itself may incorporate suitable fastenings, such as hook-and-loop or adhesive fasteners.

Use of the Dressing According to the Invention in Clinical Practice

A 44-year old man was chosen as the subject of the clinical study. He was admitted to the medical unit generally very unwell and was suffering from liver failure, cardiac myopathy, and renal failure. His lower limbs were grossly oedematous and the skin had begun to beak down in the week prior to admission. He presented with superficial ulceration to both legs which were heavily contaminated with *Pseudomonas*. Both limbs, from the level of the knees down, were leaking copious amounts of fluid, both from the ulcer beds and the skin pores. This leakage was causing maceration, increasing ulcer size and excruciating pain to the man.

A first line treatment was employed to combat the *Pseudomonas* infection but this was increasingly difficult due to the deteriorating medical condition of the patient and the fact that he was unable to tolerate most dressing/topical treatments or compression due to the levels of pain experienced. The aim of the initial management therefore was to promote comfort while preventing further maceration and subsequent ulcer expansion.

Initially, foam dressings were used, but these were unable to hold the copious amounts of fluid being expressed and required changing two or three times a day. At this point the patient remained in severe pain and the ulcer beds were increasing in size. The combination of pain and his bandages dripping within an hour of each dressing change had a considerable negative impact on the quality of life of the patient, and he found that mobilisation was impossible. A dressing according to the invention generally taking the form of the embodiment depicted in FIGS. 1 and 2 was applied and within two days the nurses reported a reduction in dressing change frequency to only once a day. They also reported that the dressing held all the exudate, with strike-through being seen only after 24 hours. Furthermore the dressings were very easy to use and dressing changes were mostly pain free.

Within five days of commencing treatment with the dressing, there was no further evidence of maceration and the ulcer edges had stopped advancing. The patient reported a significant reduction in pain levels. As the dressing was holding all the exudate, he was able to mobilise without the embarrassment and discomfort of wet bandages.

The invention claimed is:

1. A non-adhesive absorbent wound dressing for application about a jointed limb, the wound dressing having a first portion adapted to conform to and wrap around an upper part of the limb, a second portion adapted to conform to and wrap around a lower part of the limb, and a hinge portion between said first portion and said second portion, said hinge portion in use lying adjacent to the joint of the limb;

wherein the dressing comprises a porous wound contact sheet and a substantially liquid-impermeable backing sheet, the wound contact sheet and the backing sheet being bonded together at their periphery and along lines that define a plurality of pockets in both the first portion and the second portion, the pockets (i) containing a superabsorbent material and (ii) being located across substantially the entire surface of the wound contact sheet;

and wherein the hinge portion between the first and second portions comprises a bonded area which extends across the dressing, from one point on a perimeter of the dressing to another, and wherein the hinge portion is of lesser width than the first portion and the second portion.

2. An absorbent wound dressing according to claim 1, wherein the wound contact sheet comprises a woven or non-woven fabric.

3. An absorbent wound dressing according to claim 1, wherein the wound contact sheet is formed with a regular array of perforations across its full extent.

4. An absorbent wound dressing according to claim 3, wherein the perforations have a size of from 50 μm to 10 mm.

5. An absorbent wound dressing according to claim 3, wherein the perforations have a size of from 0.1 mm to 1.5 mm.

6. An absorbent wound dressing according to claim 1, wherein the backing sheet is vapour permeable.

7. An absorbent wound dressing according to claim 1, wherein the backing sheet comprises a film of plastics material, such as polyurethane or polyethylene.

8. An absorbent wound dressing according to claim 1, wherein the materials of the wound contact sheet and the backing sheet include a fusible component so that bonds can be formed by the application of heat and pressure.

9. An absorbent wound dressing according to claim 1, wherein the bonding is by adhesive or stitching.

10. An absorbent wound dressing according to claim 1, wherein the absorbent material is formed into a sheet, mat or pad.

11. An absorbent wound dressing according to claim 10, wherein the sheet, mat or pad of absorbent material is shaped and dimensioned such that it occupies substantially the whole of the pocket within which it is contained.

12. An absorbent wound dressing according to claim 1, wherein the absorbent material absorbs up to 200, 400, or 500 times or more its weight of fluid.

13. An absorbent wound dressing according to claim 1, wherein the superabsorbent material is selected from one or more polyacrylates, polyacrylamide copolymers, ethylene maleic anhydride copolymers, cross-linked carboxymethylcellulose, polyvinylalcohol copolymers, cross-linked polyethylene oxides, starch-grafted copolymers of polyacrylonitrile, and alginates.

14. An absorbent wound dressing according to claim 13, wherein the superabsorbent material is calcium alginate or sodium alginate.

15. An absorbent wound dressing according to claim 10, wherein the sheet, mat or pad is formed from a material that acts as a carrier for superabsorbent material.

16. An absorbent wound dressing according to claim 1, wherein the first and second portions each comprise at least three pockets.

17. An absorbent wound dressing according to claim 1, wherein the first and second portions each comprise no more than ten pockets.

18. An absorbent wound dressing according to claim 1, wherein the first and second portions differ in size and comprise differing numbers of pockets.

19. An absorbent wound dressing according to claim 1, wherein the areas of the first and second portions are in a ratio of less than 3:1.

20. An absorbent wound dressing according to claim 1, wherein the areas of the first and second portions are in a ratio of greater than 3:1.

21. An absorbent wound dressing according to claim 1, wherein the width of the hinge portion is up to 75% of that of the first and/or the second portion.

22. A wound dressing according to claim 1 which further comprises a carbonised deodoriser or an anti-microbial material.

23. A wound dressing according to claim 22, wherein the anti-microbial material is silver.

24. A wound dressing according to claim 1, for application about a knee joint.

25. A wound dressing according to claim 1, for application about an elbow joint.

26. A wound dressing according to claim 1, for application about a wrist joint.

* * * * *